(12) United States Patent
Ban et al.

(10) Patent No.: US 6,239,100 B1
(45) Date of Patent: May 29, 2001

(54) SYNTHETIC POLYPEPTIDE HAVING FISH GROWTH HORMONE-LIKE ACTIVITY, NUCLEIC ACID ENCODING FOR THE POLYPEPTIDE AND METHOD USING SAME

(75) Inventors: Takayuki Ban, Kasai; Yasunobu Takeshima, Kakogawa; Hideaki Hagiwara, Takarazuka, all of (JP)

(73) Assignee: HIH Biocenter INC, Hyogo (JP)

( * ) Notice: Subject to any disclaimer, the term of this patent is extended or adjusted under 35 U.S.C. 154(b) by 0 days.

(21) Appl. No.: 09/194,185

(22) PCT Filed: Mar. 23, 1998

(86) PCT No.: PCT/JP98/01230

§ 371 Date: Nov. 24, 1998

§ 102(e) Date: Nov. 24, 1998

(87) PCT Pub. No.: WO98/42748

PCT Pub. Date: Oct. 1, 1998

(30) Foreign Application Priority Data

Mar. 24, 1997 (JP) .................................................... 9/087307

(51) Int. Cl.[7] .............................. C12N 5/10; C12N 15/12; C12N 15/63; C07K 14/475; A61K 9/14
(52) U.S. Cl. .............................. 514/2; 530/350; 530/399; 536/23.1; 536/23.5; 536/23.51; 435/69.4; 435/71.1; 435/71.2; 435/471; 435/325; 435/375; 435/252.3; 435/254.11; 514/8; 514/12; 424/93.1; 424/93.2; 424/439; 424/442

(58) Field of Search ..................................... 530/350, 399, 530/23.1, 23.5, 23.51; 435/69.4, 71.1, 71.2, 471, 325, 375, 252.3, 254.11, 320.1; 514/2, 8, 12; 424/93.1, 93.2, 439, 442

(56) References Cited

FOREIGN PATENT DOCUMENTS

| 2-223596 | 9/1990 | (JP) . |
| 5-568572 | 3/1993 | (JP) . |

OTHER PUBLICATIONS

Noso, et al., Isolation and characterization of growth hormone . . . , Int. J. Peptide Protein Res., vol. 32, 1988, pp. 579–589.

Kariya, et al., Isolation and characterization of growth hormone . . . , Agric. Biol. Chem., vol. 53, No. 6, 1989, pp. 1679–1687.

Sato et al. (1988) Biochimica et Biophysica Acta 949 (1988) pp. 35–42.*

Noso et al., (1988) Int. J Peptide Protein Res. vol. 32, pp. 579–589.*

George et al., (1988)*

* cited by examiner

Primary Examiner—Prema Mertz (57) ABSTRACT

The present invention provides a novel polypeptide which has fish growth hormone-like activity and which can be widely used no matter what the species of fish is.

19 Claims, 6 Drawing Sheets

SYNTHETIC POLYPEPTIDE HAVING FISH GROWTH HORMONE-LIKE ACTIVITY, NUCLEIC ACID ENCODING FOR THE POLYPEPTIDE AND METHOD USING SAME

CROSS REFERENCE TO RELATED APPLICATION

This is a §371 of International PCT Application, PCT/JP98/01230, filed Mar. 23, 1998, and published under number WO98/42748.

TECHNICAL FIELD

This invention relates to a novel polypeptide, and more specifically to a polypeptide which shows fish growth hormone-like activity, a DNA which codes thereof, a vector which contains said DNA, a microorganism which is transformed with said vector, a preparation process of the above-mentioned peptide using said microorganism, and use of said peptide in promoting fish growth and reducing mortality of fry.

BACKGROUND ART

Growth hormones the existence of which is common to mammals, avians, reptiles, amphibians and fish are polypeptides that are secreted from the pituitary gland, and there are various reports about growth hormones that were isolated and the structure of which was determined by various research groups. Along with advances in gene engineering, mass production of these growth hormones in microorganisms has become possible and is about to be used for many kinds of livestock. Concerning fish the current situation, however, is that growth hormones are only used on research basis but not applied for practical use.

Since fish growth hormones are responsible for growth promotion of fish, it is believed that if fish growth hormones were available as fodder for hatchery fish, pre-shipment period could be shortened and that this also would be helpful for cost reduction. Natural growth hormones which have been isolated from fish, however, have species specificity to some extent, and therefore, for example, when tuna growth hormone which is commercially available as an agent is given orally to fish other than tuna, although a slight effect may be expected, the effect can not be regarded as sufficient.

Therefore, the inventors of the present application did research for developing a polypeptide which can be used for a variety of fish having universal fish growth hormone-like activity, by exerting supreme growth-promoting activity in fish.

DISCLOSURE OF INVENTION

As a result, it was found that a polypeptide with the following amino acid sequence (SEQ ID NO: 1)

```
Gln Pro Ile Thr Asp Ser Gln Arg Leu Phe Ser Ile Ala Val Ser Arg
 1               5                  10                  15
Val Gln His Leu His Leu Leu Ala Gln Arg Leu Phe Ser Asp Phe Glu
             20                  25                  30
Ser Ser Leu Gln Thr Glu Glu Gln Arg Gln Leu Asn Lys Ile Phe Leu
         35                  40                  45
Gln Asp Phe Cys Asn Ser Asp Tyr Ile Ile Ser Pro Ile Asp Lys His
     50                  55                  60
Glu Thr Gln Arg Ser Ser Val Leu Lys Leu Leu Ser Ile Ser Tyr Arg
 65                  70                  75                  80
Leu Val Glu Ser Trp Glu Phe Pro Ser Arg Ser Leu Ser Gly Gly Ser
                 85                  90                  95
Ala Pro Arg Asn Gln Ile Ser Pro Lys Leu Ser Glu Leu Lys Met Gly
            100                 105                 110
Ile His Leu Leu Ile Arg Ala Asn Gln Asp Gly Ala Glu Met Phe Ala
            115                 120                 125
Asp Ser Ser Ala Leu Gln Leu Ala Pro Tyr Gly Asn Tyr Tyr Gln Ser
    130                 135                 140
Leu Gly Gly Asp Glu Ser Leu Arg Arg Asn Tyr Glu Leu Leu Ala Cys
145                 150                 155                 160
Phe Lys Lys Asp Met His Lys Val Glu Thr Tyr Leu Arg Val Ala Lys
                165                 170                 175
Cys Arg Leu Ser Pro Glu Ala Asn Cys Thr Leu
                180                 185
``` shows growth hormone-like activity, and displays remarkable growth-promoting and fry mortality-reducing effects in a variety of fish.

Therefore, the aim of this invention is to provide a polypeptide which comprises the above-mentioned amino acid sequence, or an amino acid sequence of which one or more amino acid(s) of the above-mentioned amino acid sequence is/are deleted, substituted or added, and which also shows fish growth hormone activity.

The polypeptide of this invention can be chemically synthesized by a solid phase method or a liquid phase method which is known per se, or biochemically synthesized by means of gene engineering technique using a DNA which codes the polypeptide of this invention.

BRIEF DESCRIPTION OF DRAWINGS REFERRED TO IN THE FOLLOWING EXAMPLES

Figure 1:
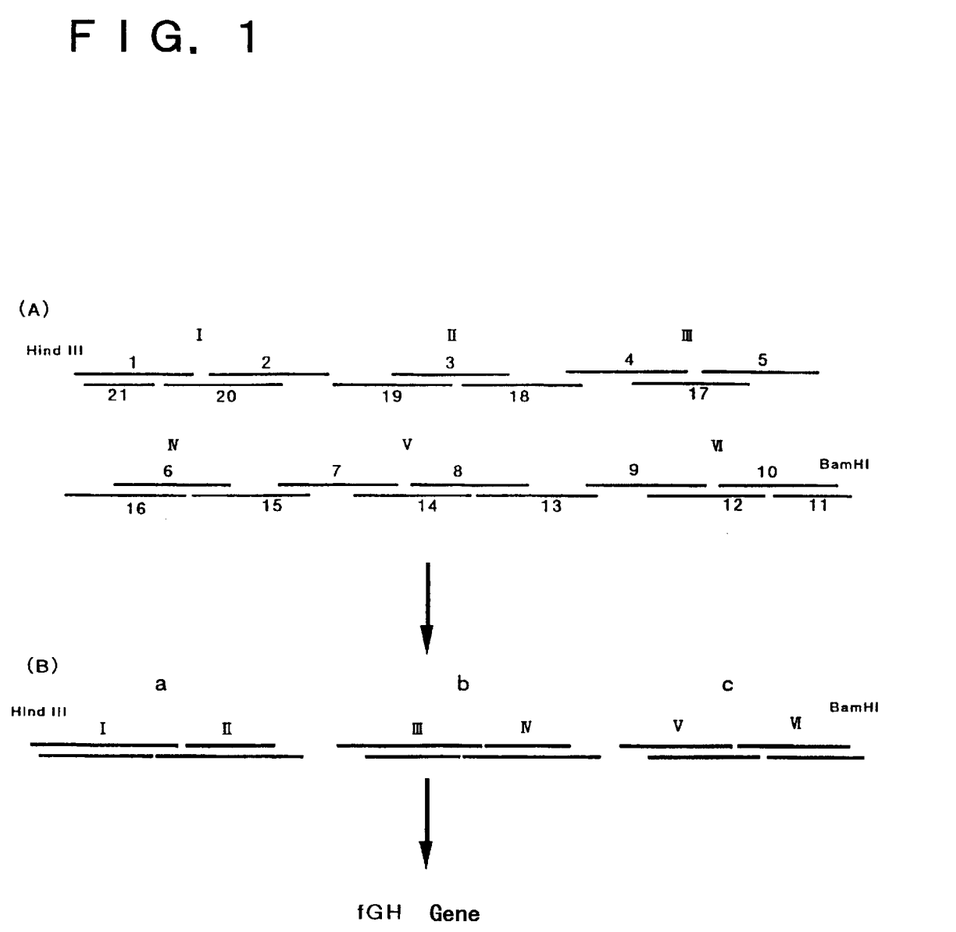

FIG. 1 is a process drawing to show the process to construct fGH gene of this invention.

Figure 2:
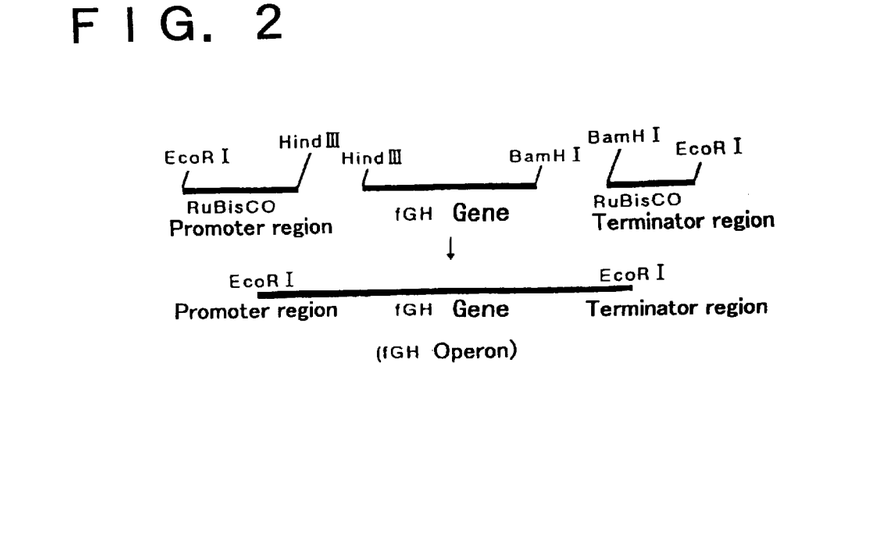

FIG. 2 is a process drawing to show the process to generate fGH operon.

Figure 3:
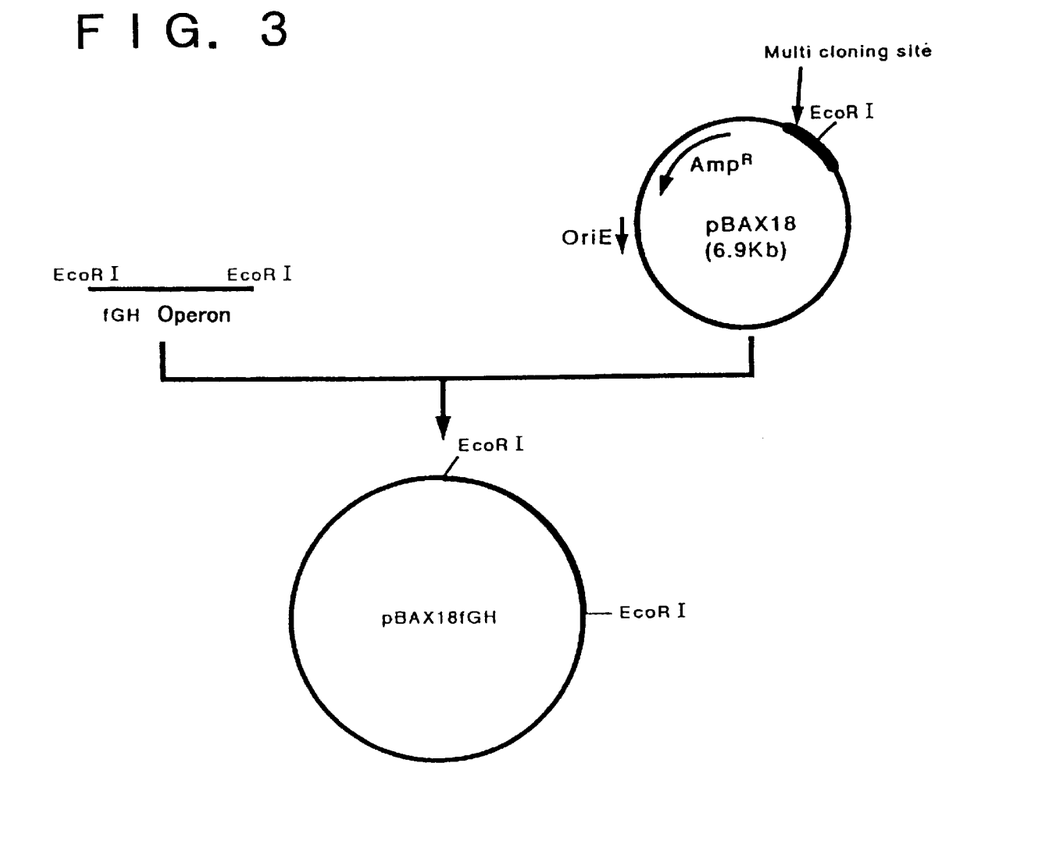

FIG. 3 is a process drawing to show the process of the integration of fGH operon into a multi cloning site of a *Escherichia coli*—Cyanobacterium shuttle vector pBAX18.

Figure 4:
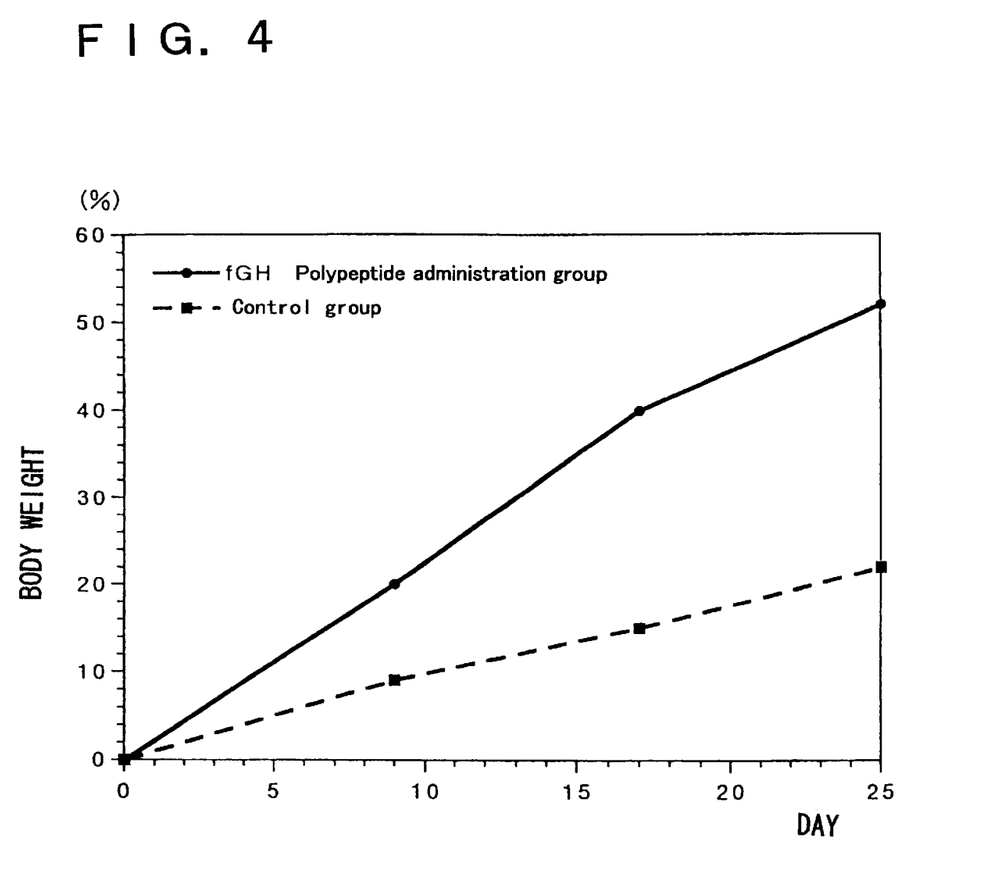

FIG. 4 is a graph to show the growth-promoting effect of fGH polypeptide of Example 1 on carp fry.

Figure 5:
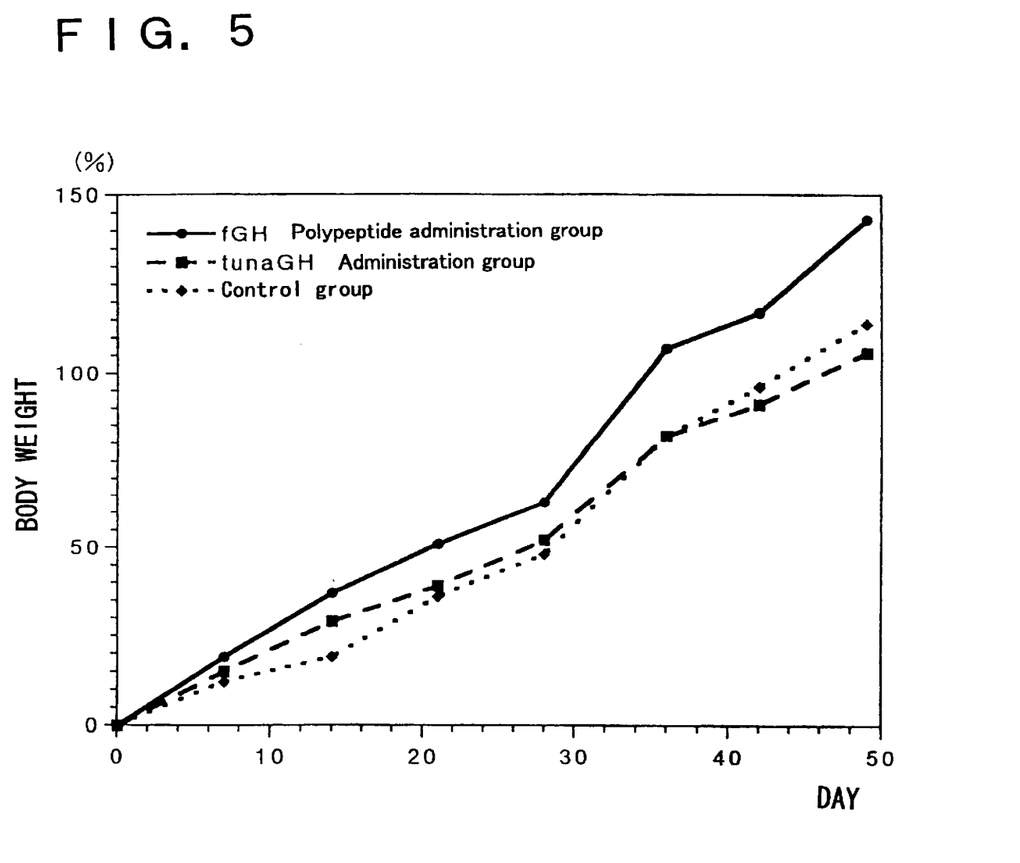

FIG. 5 is a graph to show the growth-promoting effect of fGH polypeptide of Example 2 on tuna fry.

Figure 6:
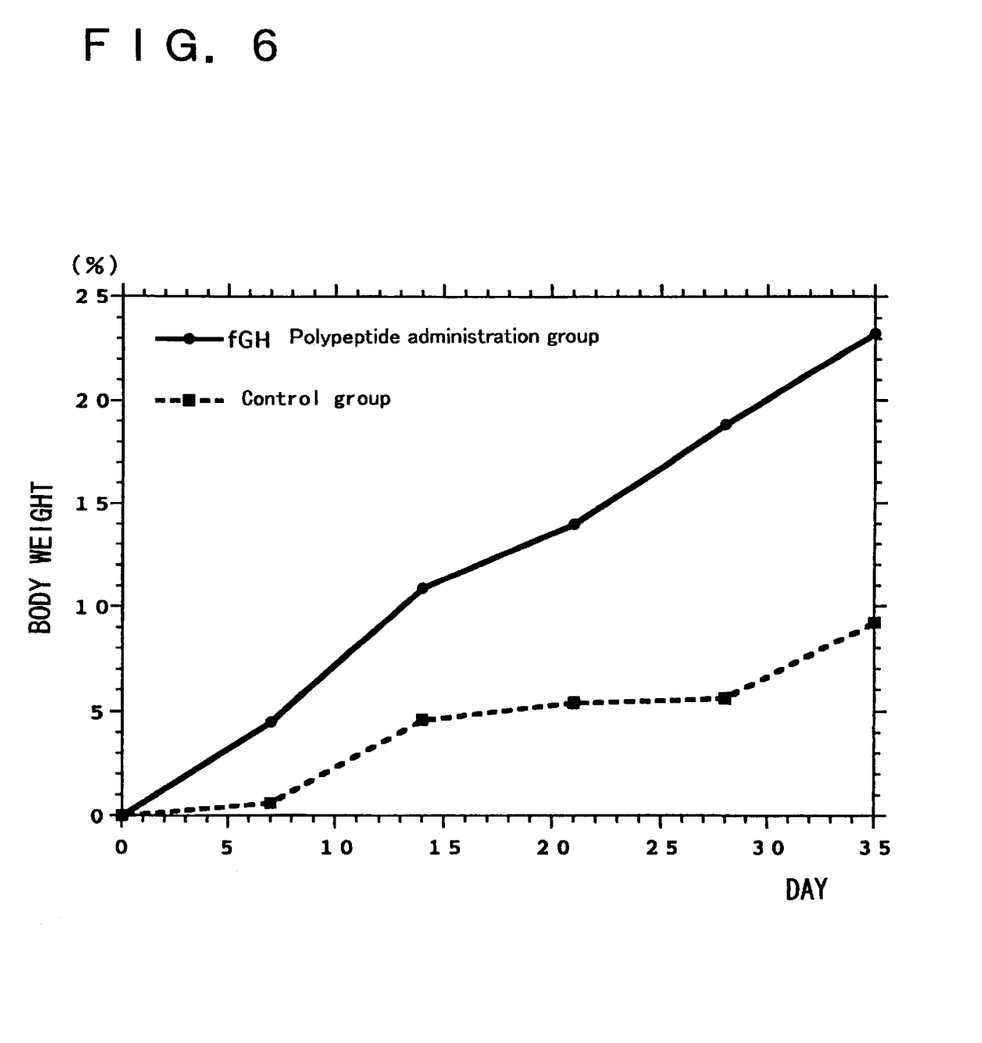

FIG. 6 is a graph to show the growth-promoting effect of fGH polypeptide of Example 5 on Aulonocara fry.

Figure 7:
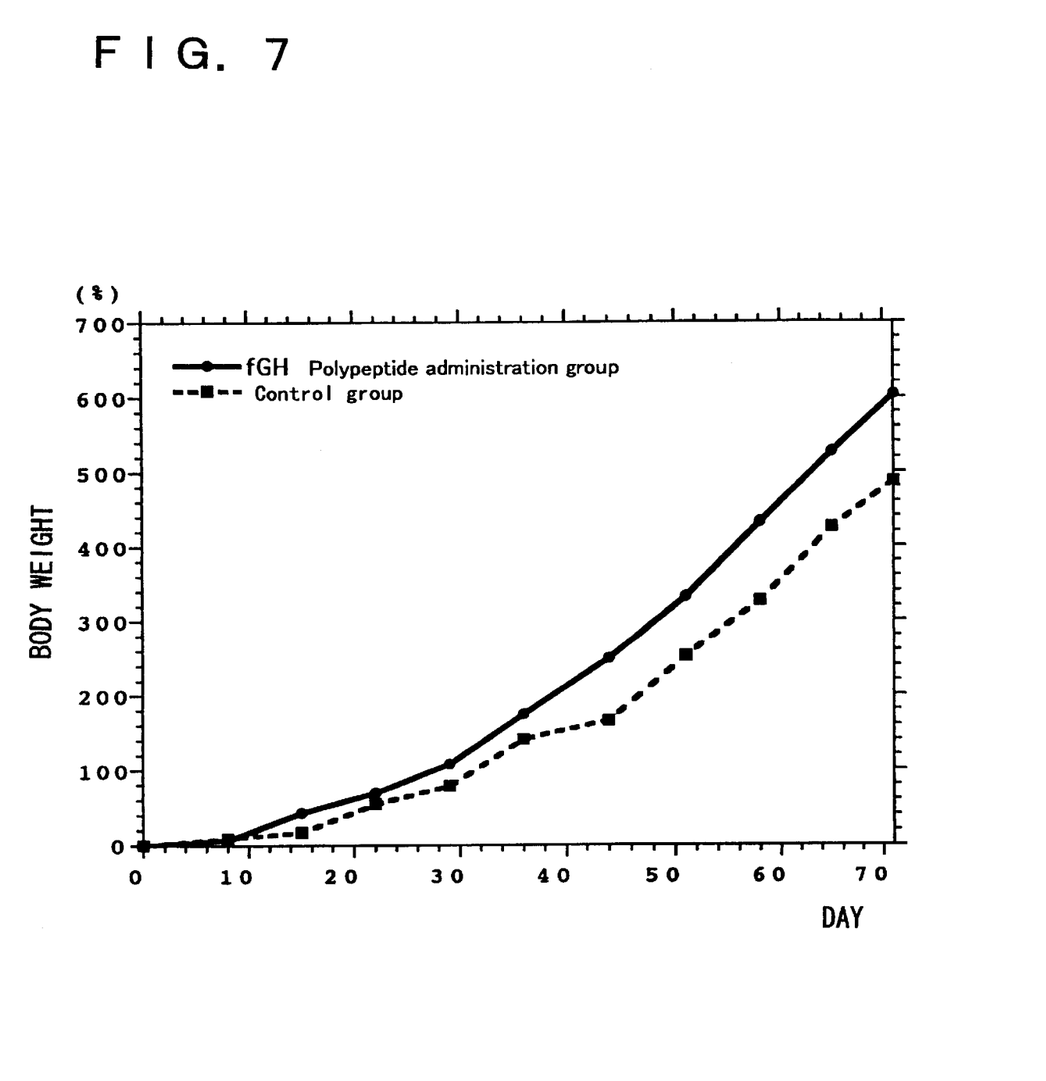

FIG. 7 is a graph to show the growth-promoting effect of fGH polypeptide of Example 6 on angelfish fry.

MODE FOR CARRYING OUT THE INVENTION

A case where the polypeptide of this invention is biochemically synthesized by means of gene engineering technology will be illustrated with Examples hereinafter.

(1) Synthesis of Oligonucleotides

With taking account of frequency of codons used with Cyanobacterium as a host, a DNA fragment which encodes the polypeptide with the above-mentioned amino acid sequence (which is referred to as fGH polypeptide hereinafter) is designed (this DNA is referred to as fGH gene hereinafter).

The base sequence of the designed DNA fragment (SEQ ID NO: 2) is as follows.

Next, the fragments I–VI synthesized in this way are ligated to three fragments a (I+II), b (III+IV), and c (V+VI) (see FIG. 1 (B)). In short, 2 µg each of fragments I–VI are dissolved in 40 µl ligation buffer, then after incubation at 37° C. for 30 minutes, cooled slowly to 4° C. over a period of 30 minutes, 5 µl each of 100 mM DTT and 10 mM ATP (manufactured by Pharmacia Inc.) and moreover 10 units of T4 DNA ligase (manufactured by Takara Co., Ltd.) are added, and then incubated at 4° C. for 16 hours. Hereafter, these solutions are treated with equal volumes of phenol-chloroform and chloroform, and then DNAs are collected by ethanol precipitation.

Finally, 2 µg each of the resulting fragments a–c are dissolved in 40 µl ligation buffer, after incubation at 37° C. for 30 minutes, cooled slowly to 4° C. over a period of 30 minutes, 5 µl each of 100 mM DTT and 10 mM ATP (manufactured by Pharmacia Inc.) and moreover 10 units of T4 DNA ligase (manufactured by Takara Co., Ltd.) are added, and then incubated at 4° C. for 16 hours. Hereafter,

```
CAGCCTATTA CCGATTCTCA GCGTCTGTTC TCTATTGCTG TTTCTCGTGT TCAGCACCTG  60
CACCTGCTGG CGCAGCGTCT GTTCTCTGAT TTTGAATCTT CTCTGCAAAC CGAAGAACAG 120
CGTCAGCTGA ACAAAATTTT CCTGCAGGAT TTCTGTAACT CTGATTACAT TATTTCTCCT 180
ATTGATAAAC ACGAAACTCA GCGTTCTTCT GTTCTGAAAC TGCTGTCTAT TTCTTACCGT 240
CTGGTTGAAT CTTGGGAATT CCCTTCTCGT TCTCTGTCTG GTGGTTCTGC TCCTCGTAAC 300
CAGATTTCTC CTAAACTGTC CGAGCTCAAA ATGGGTATTC ACCTGCTGAT TCGTGCTAAC 360
CAGGATGGTG CTGAAATGTT CGCTGATTCT TCTGCTCTGC AGCTCGCTCC TTACGGTAAC 420
TACTACCAGT CTCTGGGTGG TGATGAATCT CTGCGTCGTA ACTACGAACT GCTGGCTTGT 480
TTCAAAAAAG ATATGCACAA AGTTGAAACC TACCTGCGTG TCGCGAAATG TCGTCTGTCT 540
CCTGAAGCTA ACTGCACCCT G                                         561
```

The designed DNA is divided into several blocks, for example, into twenty-one blocks of about sixty bases each (see FIG. 1 (A)), and then the oligonucleotide of each block is synthesized by means of phosphoamidite method using a DNA synthesizer.

(2) Phosphorylation of Synthetic Oligonucleotide by a Kinase

Three µg of each of the synthesized oligonucleotides (except for No. 1 and No. 11) is incubated using 2 µL of Takara kination kit (oligonucleotide 3 µl, 10×kination buffer 2 µl, 100 mM ATP (manufactured by Pharmacia Inc.), polynucleotide kinase 1 µl (10 units), and sterile water 12 µl) at 37° C. for 90 minutes. After the reaction, the enzyme is deactivated through heat treatment at 90° C. for 5 minutes, and then phenol-chloroform treatment and chloroform treatment are conducted. The phosphorylated oligonucleotide is collected by ethanol precipitation using Ethanol Precipitation Mate (manufactured by Nippon Gene Co.).

(3) Preparation of fGH Gene

The phosphorylated oligonucleotide which is collected is divided into six groups I–VI of three or four each (see FIG. 1 (A)), then annealed. The oligonucleotides of each group are ligated by means of T4 DNA ligase to synthesize six fragments I–VI.

In other words, in the case of an oligonucleotide which is located at the 5' end among the oligonucleotides which consist of the fragment I, 1.5 µg is dissolved in 80 µl of a ligation buffer and in the other case, 1.0 µg is dissolved in 80 µl of the ligation buffer. This solution is heated at 90° C. for five minutes, cooled slowly to 4° C. over a period of 2 hours, 10 µl each of 100 mM DTT and 10 mM ATP (manufactured by Pharmacia Inc.) and moreover 2.5 units of T4 DNA ligase (manufactured by Takara Co., Ltd.) are added, and then incubated at 4° C. for 16 hours. Hereafter, the solution is treated with equal volumes of phenol-chloroform and chloroform, and DNAs are collected by ethanol precipitation. Fragments II–VI are synthesized by the same ligation reaction and collected.

these solutions are treated with equal volumes of phenol-chloroform and chloroform, and then DNAs are collected by ethanol precipitation. The DNAs are loaded on an agarose electrophoresis, a band of the same size as the initially designed DNA fragment is cut out, and then fGH gene is collected.

(4) Hind III/Bam HI Digestion and Dephosphorylation of plasmid DNA (pUC18)

An Eppendorf tube in which 2 µl of 10×K buffer, 10 units of Hind III (1 µl), 10 units of Bam HI (1 µl) and sterile water are added to 10 µg of plasmid DNA (pUC18) (10 µl) to 20 µl in total is incubated at 37° C. for one hour. Hereafter, the reaction solution is subjected to agarose electrophoresis, and the band of interest is cut out from the gel and collected. The collected DNA is dissolved in 100 µl of 100 mM Tris-HCl (pH 8.0), to which 5 units of alkaline phosphatase (1 µl) are added and incubated at 37° C. for 60 minutes. Then again 5 units of alkaline phosphatase (1 µl) are added and incubated at 65° C. for 15 minutes. The reaction solution is subjected to phenol-chloroform and chloroform treatments, and DNAs are collected by ethanol precipitation and then dissolved in 5 µl of 100 mM Tris-HCl (pH 7.6) and 5 mM $MgCl_2$ in total.

(5) Insertion of fGH Gene into pUC18

100 ng (2 µl) of fGH gene which is obtained in the above (3) and 200 ng (3 µl) of pUC18 (Hind III/Bam HI) which is obtained in the above (4) are placed into an Eppendorf tube, and then 20 µl of Takara Ligation Kit A Solution are added and mixed well. To the mixed solution, 5 µl of Takara Ligation Kit B Solution is added and after mixing, subjected to reaction at 16° C. for 90 minutes.

(6) Transformation of Escherichia coli (JM109)

To 100 µl of competent cell JM109 (manufactured by Nippon Gene Co.) which is thawed on ice, 10 µl of the ligation solution obtained in the above (5) is added and gently mixed. The mixed solution is incubated on ice for 30 minutes, further incubated at 42° C. for 45 seconds and then again incubated on ice for 3 minutes so that the DNAs are incorporated into the cells. To the suspension, 400 μl of medium (Hi-competence Broth) is added and then plated onto 1.5% LB agar medium (50 μg/ml ampicillin, 40 mg/1× gal, 23.38 mg/1 IPTG) after shake culture at 37° C. for 60 minutes. From the resulting white colonies, plasmids are prepared, a part of which are digested with Hind III and Bam HI to confirm insertion, and then colonies which hold the DNA of the plasmid of interest (fGH gene) are screened. Screened colonies are cultured in 100 ml of LB medium (50 μg/ml ampicillin) and the plasmid DNA is prepared in large amounts by means of SDS-alkaline process.

(7) Large amount Preparation of fGH Gene

An Eppendorf tube in which 2 μl of 10×K buffer, 12 units of Hind III (1 μl), 12 units of Bam HI (1μl) and sterile water are added to 10 μg of plasmid DNA (fGH gene) (10 μl) prepared in large amounts according to the above (6) to 20 μl in total is incubated at 37° C. for two hours. After the reaction, phenol-chloroform and chloroform treatments are conducted, and then DNAs are collected by conducting ethanol precipitation and dissolved in 10 μl of sterilized water. Hereafter, the DNAs are separated by means of 1% agarose electrophoresis and the DNA fragment of interest is electrically extracted from the gel which is cut out. The extracted solution is concentrated with butanol, and after phenol-chloroform and chloroform treatments, the DNAs are collected by ethanol precipitation.

(8) Massive Preparation of RuBisCO Promoter and Terminator Regions of *Anacystis Nidulans*

*Escherichia coli* which holds plasmids (pARup18, pARut13) which contains RuBisCO promoter and terminator regions, respectively, of *Anacystis nidulans* (Takeshima, Y., Sugiura, M., and Hagiwara, H., 1994, A novel expression vector for the Cyanobacterium, Synechococcus PCC6301, DNA Research 1, 181–189) is cultured in 100 ml of circle growth medium, and the plasmid DNAs are prepared in large amounts by means of SDS-alkaline method. pARup18 is digested with Eco RI and Hind III, while pARut18 is digested with Eco RI and Bam HI. After the reaction, the DNA fragment of interest is separated by 3% agarose gel electrophoresis and then the band is cut out and electrically extracted. The extracted solution is concentrated with butanol, and after phenol-chloroform and chloroform treatments, the DNAs are collected by ethanol precipitation.

(9) Methylation of Eco RI Sites of fGH Gene

An Eppendorf tube in which 10 μl of 500 mM Tris-HCl (pH 8.0), 1 μl of 100 mM DTT, 30 units of Eco RI methylase (0.5 μl), 2 μl of 3.2 mM S-adenosyl methionine and 31.5 μl of sterile water are added to 5 μl of fGH gene (5 μg) is incubated at 37° C. for one hour, and after phenol-chloroform and chloroform treatments, the DNAs are collected by ethanol precipitation. The precipitate is dissolved in 5 μl of 100 mM Tris-HCl (pH 7.6) and 5 mM MgCl$_2$ in total.

(10) Preparation of fGH Operon (see FIG. 2)

One μg (2 μl) of fGH gene prepared in large amounts according to the above (9) (with Eco RI sites already methylated) and 1 μg (2 μl) each of the RuBisCO promoter and terminator regions of *Anacystis nidulans* prepared in the above (8) are placed in an Eppendorf tube, and then 24 μl of Takara Ligation Kit A Solution is added and mixed well. To this mixed solution, 6 μl of Takara Ligation Kit B Solution is added and after mixing, the mixture is subjected to reaction at 16° C. for 90 minutes. After the reaction is completed, and phenol-chloroform and chloroform treatments, DNAs are collected by ethanol precipitation. Hereto, 17 μl of sterile water, 2 μl of 10×H buffer and 1 μl of Eco RI are added, and then incubated at 37° C. for one hour.

(11) Digestion with Eco RI and Dephosphorylation of Plasmid DNA (pBAX18)

An Eppendorf tube in which 2 μl of 10×H buffer, 12 units of Eco RI (1 μl) and sterile water are added to 10 μg of plasmid DNA (pBAX18-Deposit Number FERM BP-4639) (10 μl) to 20 μl in total is incubated at 37° C. for one hour. Hereafter, the reaction solution is subjected to agarose electrophoresis, and then the band of interest is cut out and collected from the gel. The collected DNA is dissolved in 100 μl of 100 mM Tris-HCl (pH 8.0), 5 units of alkaline phosphatase (1 μl) are added and incubated at 37° C. for 60 minutes. Then again 5 units of alkaline phosphatase (1 μl) are added and incubation is carried out at 65° C. for 15 minutes. The reaction solution is treated with phenol-chloroform and chloroform, then the DNAs are collected by ethanol precipitation, and dissolved in 5 μl of a solution consisting of 100 mM Tris-HCl (pH 7.6) and 5 mM MgCl$_2$.

(12) Ligation of fGH Operon and pBAX18 (which has been already digested with Eco RI and dephosphorylated) (see FIG. 3)

One μg (2 μl) each of the fGH operon which is prepared in the above (10) and the plasmid DNA which is obtained in the above (11) are placed into an Eppendorf tube, and then 24 μl of Takara Ligation Kit A Solution is added and mixed well. To the mixed solution, 6 μl of Takara Ligation Kit B Solution is added and after mixing, subjected to reaction at 16° C. for 90 minutes.

(13) Transformation of *Escherichiai Coli* (JM109)

To 100 μl of competent cell JM109 (manufactured by Nippon Gene Co.) which is thawed on ice, 10 μl of the ligation solution which is obtained in the above (12) are added and gently mixed. The mixed solution is incubated on ice for 30 minutes, and then incubated at 42° C. for 45 seconds and again incubated on ice for three minutes so that the DNAs are incorporated into the cells. To the suspension, 400 μl of Hi-competence Broth is added, and then, after shake culture at 37° C. for 60 minutes, plated onto 1.5% LB agar medium (50 μg/ml ampicillin, 40 mg/1×gal, 23.38 mg/1 IPTG). From the resulting white colonies, plasmids are prepared a part of which is digested with Eco RI to confirm the insert and then the colonies which hold the expression vector of interest (pBAX18fGH) are screened. The screened colonies are cultured in 100 ml of LB medium (50 μg/ml ampicillin) and plasmid DNAs are prepared in large amounts by means of SDS-alkaline method.

(14) Expression of fGH Gene by Cyanobacterium (*Anacystis nidulans* PCC6301 old strain-Deposit Number FERM BP-6267; ATCC 27144)

*Anacystis nidulans* PCC6301 old which has been cultured in 100 ml of BG-11 liquid medium for about one week is collected by centrifugation at 8000 rpm for 5 minutes, and then suspended in 10 ml of fresh liquid medium ($10^8$–$10^9$ cells/ml). This cell suspension is fractionated into aliquots. of one ml, placed into polypropylene tubes, and then to each tube, the expression DNA which is prepared in the above (13) is added at concentrations of 0.1–10 μg. These tubes are covered with aluminum foil, and uncovered after overnight incubation at 25° C., after which incubation is carried out under light illumination (light source: white fluorescent lamp; 1000–2000 lux) for further 6 hours. From each of these cell suspensions, 100–500 μl are removed and plated on BG-11 medium (1 mM sodium thiosulfate, 5 μg/ml ampicillin, 1.5% agar). These plates are cultured under light illumination (light source: white fluorescent lamp; 1000–2000 lux) for 4–10 days.

The colonies obtained in this way are transferred into 2 ml of BG-11 liquid medium (10 μg/ml ampicillin) and cultured under light illumination (light source: white fluorescent lamp; 1000–2000 lux) for 10 days. Then, this culture solution is transferred into 100 ml of BG-11 liquid medium (50 μg/ml ampicillin) and cultured under light illumination (light source: white fluorescent lamp; 1000–2000 lux) for 10 days. Cells are collected by centrifugation at 10,000 rpm at 4° C. for 10 minutes, suspended in 10 mM PBS, and washed by centrifuging again. After washing, cells are stored at −20° C. until use.

(15) Confirmation of fGH Gene Expression by Means of RT-PCR method

The transformant and non-transformant of *Anacystis nidulans* which are cultured in 100 ml BG-11 medium are separately centrifuged and collected, 90 mg each are suspended in 1 ml of isogene (manufactured by Nippon Gene Co.) and incubated at room temperature for 10 minutes. To each suspension, 0.2 ml chloroform is added and incubated at room temperature for 5 minutes after vigorous shaking for 15 seconds. Hereafter, suspensions are centrifuged at 15,000 rpm and 4° C. for 15 minutes, the aqueous layers are transferred into new tubes, to each of which 0.5 ml of isopropanol is added, and then incubated at room temperature for 10 minutes. Hereafter, centrifugation at 15,000 rpm and 4° C. for 15 minutes carried out, and after discarding supernatants and gentle washing with 70% ethanol, fractions are shortly dried and dissolved in RNase-free water. The fractions obtained are regarded as total RNA fractions. Hereafter, RT-PCR is performed using these total RNA fractions and Definitive RT-PCR KIT (manufactured by Biotech International). As a result of agarose electrophoresis of these PCR products, a band could be confirmed at the expected position (about 600 bp) for the transformant. This indicates that the gene which is introduced in the transformed *Anacystis nidulans* is precisely expressed.

(16) Confirmation of fGH Polypeptide Expression of this Invention by Means of SDS-PAGE (SDS polyacrylamide gel electrophoresis)

The transformant and non-transformant of *Anacystis nidulans* which were cultured in 100 ml BG-11 medium were separately centrifuged and then subjected to SDS-polyacrylamide gel electrophoresis according to Laemmli's method. After electrophoresis, they were dyed with Coomassie Brilliant Blue and a band of the polypeptide was detected at the position of the expected molecular weight of about 24,000. This band did not exist when the non-transformant was subjected to SDS-polyacrylamide gel electrophoresis. Moreover, when transfering this band to a PVDF membrane and determining the amino acid sequence by a vapor phase sequencer type 477A/120A of Applied Biosystems Co., the amino acid sequence of the polypeptide of this band was completely consistent with the amino acid sequence of the abovementioned fGH polypeptide of this invention. This shows that Cyanobacterium *Anacystis nidulans* holding pBAX18fGH, expresses fGH polypeptide of this invention.

A deposit of *Anacystis nidulans* PCC 6301 old strain, transformed with pBAX18fGH, was deposited, on Nov. 15, 2000, at National Institute of Bioscience and Human-Technology Agency of Industrial Science and Technology (NIBH), whose address is 1-3, Higashi 1-chome, Tsukuba-shi, Ibaraki-ken 305-8566, JAPAN. NIBH is a Japanese authorized depository. The deposit was made under the Budapest Treaty, and was assigned deposit number FERM BP-7367.

fGH polypeptide of this invention which is generated according to the above description has remarkable effects on growth-promotion and also in regard to mortality reduction in a variety of fish, especially fry as shown in Examples described hereinafter, so that it can be widely used as a universal fish growth hormonal agent for promoting growth of hatchery fish (for example, freshwater fish such as carp, crucian, eel, trout, tilapia and the like; sea-water fish such as sea bream, young yellowtail, tuna, flounder (Paralichthys), place, and the like) and aquarium fish (for example, goldfish, guppy, angelfish, Aulonocara, and the like) and/or for reducing mortality of fry.

fGH polypeptide of this invention does not necessarily have to be used in its isolated and purified form, but can also be used as crude preparation, or in form of cultured dry bacterial cells itself which contain fGH polypeptide of the above-mentioned transformant.

Concerning usage of fGH polypeptide of this invention, for example, bacterial cells containing this polypeptide can be given to fish by mixing with a conventional fish feed in a dispersive way, but can also be given to fish separately along with a conventional fish feed.

TEST EXAMPLES

Fish growth-promoting effect and fry mortality-reducing effect of fGH polypeptide of this invention will be illustrated more specifically in the Test Examples hereinafter.

Test Example 1

Carp Growth Test No. 1

Fifteen carps each which were 2–3 months of age after hatching were placed into a fish tank (60 cm×cm×30 cm), and fed with normal commercially available carp feed three times a day in amounts of 100 mg/fish/time and also with a feed which was mixed with fGH polypeptide of this invention (1 mg/fish of freeze-dried *Anacystis nidulans* PCC6301old transformant, which corresponded to 1 μg/fish of fGH polypeptide of this invention) was given once a week (fGH polypeptide administration group). Moreover, to carps of the control group, a commercially available carp feed was given three times a day in amounts of 100 mg/fish/time and also a feed which was mixed with 1 mg/fish of freeze-dried *Anacystis nidulans* PCC6301old non-transformant was given once a week. Rearing was conducted between 24° C. and 26° C. Increased amounts in body weight at Day 25 after first administration were determined (as average of 15 fish) and the result is shown in Table 1 described hereinafter. Moreover, FIG. 4 shows a graph which derived by plotting the rates of increase in body weight (%) during the rearing period.

TABLE 1

| Group | Body Weight at Day 1 (g) | Body Weight at Day 25 (g) | Increased Body Weight (g) |
|---|---|---|---|
| fGH polypeptide Administration Group | 5.0 | 7.6 | 2.6 ± 0.64* |
| Control group | 5.5 | 6.7 | 1.2 ± 0.60* |

*Standard error

Test Example 2

Carp Growth Test No. 2

Five carps each which were 4–5 months of age after hatching were placed into a fish tank (90 cm×40 cm×40 cm), and fed with normal commercially available carp feed three times a day at 0.5 g/fish/time and also with a feed which was mixed with fGH polypeptide of this invention (1 mg/fish of freeze-dried *Anacystis nidulans* PCC6301old transformant, which corresponded to 1 μg/fish of fGH polypeptide of this invention) was given once a week (fGH polypeptide administration group). Moreover, to carps of the tuna GH administration group, a commercially available carp feed was given three times a day at 0.5 g/fish/time and also a feed which was mixed with 1 mg/fish of freeze-dried *Anacystis nidulans* PCC6301old non-transformant and 1 μg/fish of a commercially available tuna growth hormone (tuna GH; manufactured by Maruha) was given once a week. Moreover, to carps of the control group, a commercially available carp feed was given three times a day at 0.5 g/fish/time and also a feed which was mixed with 1 mg/fish of freeze-dry *Anacystis nidulans* PCC6301old non-transformant was given once a week. Rearing was conducted between 24° C. and 26° C. Increased amounts in body weight at Day 49 after the first administration were measured (as averages of 5 fish) and the results are shown in Table 2 described hereinafter. Moreover, FIG. 5 shows a graph which derived by plotting the rates of increase in body weight (%) during the rearing period.

TABLE 2

| Group | Body Weight at Day 1 (g) | Body Weight at Day 49 (g) | Increased Body Weight (g) |
|---|---|---|---|
| fGH polypeptide Administration Group | 26.6 | 64.5 | 37.9 ± 6.3* |
| tuna GH administration Group | 28.7 | 59.2 | 30.4 ± 2.9* |
| Control group | 26.4 | 56.5 | 30.2 ± 1.0* |

*Standard error

Test Example 3

Guppy Growth Test No. 1

Ten guppies each which were about 10–20 days of age after hatching were placed into a fish tank (60 cm×30 cm×30 cm), and fed with a guppy feed (which was prepared in Feed Preparation Example 2 described hereinafter) which was mixed with fGH polypeptide of this invention (3 mg/fish of freeze-dried *Anacystis nidulans* PCC6301old transformant, which corresponded to 3 μg/fish/day of fGH polypeptide of this invention) in amounts of 100 mg/10 fish/day. For rearing of the guppy control group, instead of *Anacystis nidulans* PCC6301old transformant, *Anacystis nidulans* PCC6301old non-transformant was used. Rearing of guppies was conducted between 25° C. and 27° C. Frequency distribution in terms of body length at Day 33 after first administration is shown in Table 3 described hereinafter.

TABLE 3

| | | Frequency | |
|---|---|---|---|
| Grade | Class (cm) | A | B |
| 1 | 1.7–2.0 | 0 | 2 |
| 2 | 2.0–2.3 | 0 | 4 |
| 3 | 2.3–2.6 | 1 | 3 |
| 4 | 2.6–2.9 | 2 | 1 |

TABLE 3-continued

| | | Frequency | |
|---|---|---|---|
| Grade | Class (cm) | A | B |
| 5 | 2.9–3.2 | 5 | 0 |
| 6 | 3.2–3.5 | 2 | 0 |

A: Group to which fGH polypeptide of this invention was administered
B: Control group Test Example 4

Guppy Growth Test No. 2

Ten guppies each which were about 10–20 days of age after hatching were placed into a fish tank (60 cm×30 cm×30 cm), and fed with a guppy feed which was mixed with fGH polypeptide of this invention (1 mg/fish of freeze-dried *Anacystis nidulans* PCC6301old transformant, which corresponded to 1 μg/fish/day of fGH polypeptide of this invention) in amounts of 100 mg/10 fish/day. The fGH polypeptide containing feed was prepared by well kneading 0.1 g of freeze-dried *Anacystis nidulans* PCC6301old transformant and water with 0.9 g of a guppy feed (manufactured by Kyorin Co.) and smashing into fine pieces in a mortar after freeze-drying. Guppies of the control group were reared using, instead of *Anacystis nidulans* PCC6301old transformant, its non-transformant form. The feed prepared was divided into portions of 100 mg each and stored at −20° C. until use. Rearing of guppies was conducted between 25° C. and 27° C. Frequency distribution in terms of body length at Day 35 after first administration is shown in Table 4 described hereinafter.

TABLE 4

| | | Frequency | |
|---|---|---|---|
| Grade | Class (cm) | A | B |
| 1 | 1.4–1.7 | 0 | 2 |
| 2 | 1.7–2.0 | 0 | 2 |
| 3 | 2.0–2.3 | 3 | 3 |
| 4 | 2.3–2.6 | 4 | 3 |
| 5 | 2.6–2.9 | 2 | 0 |
| 6 | 2.9–3.2 | 1 | 0 |

A: Group to which fGH polypeptide of this invention was administered
B: Control group Test Example 5

Aulonocara Rearing Test

Six Aulonocara (Aulonocara) each which were about 4–5 months of age after hatching were placed into a fish tank (60 cm×30 cm×30 cm), and fed with a Symphysodon (Discus) feed (manufactured by Tetra Werke Co.) which was mixed with fGH polypeptide of this invention (3 mg/fish of freeze-dried *Anacystis nidulans* PCC6301old transformant, which corresponded to 3 μg/fish/day of fGH polypeptide of this invention) in amounts of 200 mg/10 fish/day. Aulonocaras of the control group were reared using, instead of Anacystis nidulans PCC6301old transformant, its non-transformant form. Rearing of Aulonocara was conducted between 25° C. and 27° C. Increased amounts in body weight at Day 42 after first administration were determined (as averages of 6 fish) and the results are shown in Table 5 described hereinafter. Moreover, FIG. 6 shows a graph which derived by plotting rates of increase in body weight (%) during the rearing period.

TABLE 5

| Group | Body Weight at Day 1 (g) | Body Weight at Day 42 (g) | Increased Body Weight (g) |
|---|---|---|---|
| fGH polypeptide Administration Group | 4.32 | 5.98 | 1.66 ± 0.15* |
| Control group | 4.44 | 5.45 | 1.01 ± 0.24* |

*Standard error

Test Example 6

Angelfish Rearing Test

Fifteen angelfish (Pterophyllum) each which were about 3–4 months of age after hatching were placed into a fish tank (60 cm×30 cm×30 cm), and fed with a Symphysodon (Discus) feed (manufactured by Tetra Werke Co.) which was mixed with fGH polypeptide of this invention (1 mg/fish of freeze-dried Anacystis nidulans PCC6301old transformant, which corresponded to 1 µg/fish/day of fGH polypeptide of this invention) in amounts of 100 mg/fish/day. Angelfish of the control group were reared using, instead of Anacystis nidulans PCC6301old transformant, its non-transformant form. Rearing of angelfish was conducted between 25° C. and 27° C. Increased amounts in body weight at Day 71 after first administration were determined (as averages of 15 fish) and the results are shown in Table 6 described hereinafter. Moreover, FIG. 7 shows a graph which derived by plotting rates of increase in body weight (%) during the rearing period.

TABLE 6

| Group | Body Weight at Day 1 (g) | Body Weight at Day 71 (g) | Increased Body Weight (g) |
|---|---|---|---|
| fGH polypeptide Administration Group | 0.71 | 4.97 | 4.26 |
| Control group | 0.75 | 4.42 | 3.67 |

*Standard error

Test Example 7

Guppy Survival Test No. 1

Forty-three guppies each which were about 10 days of age after hatching were placed into a fish tank (60 cm×30 cm), and fed with a commercially available feed which was mixed with fGH polypeptide of this invention (1 mg/fish of freeze-dried Anacystis nidulans PCC6301old transformant, which corresponded to 1 µg/fish/day of fGH polypeptide of this invention) in amounts of 10 mg/fish/day. Guppies of the control group were reared using, instead of Anacystis nidulans PCC6301old transformant, its non-transformant form. Rearing of guppies was conducted between 25° C. and 27° C. The survival rates between first administration and day 35 are shown in Table 7 described hereinafter.

TABLE 7

| Day | A (%) | B (%) |
|---|---|---|
| 0 | 100 | 100 |
| 8 | 95.4 | 76.7 |
| 15 | 76.7 | 58.1 |
| 21 | 74.4 | 55.8 |
| 28 | 74.4 | 48.8 |
| 35 | 72.1 | 44.2 |

A: Group to which fGH polypeptide of this invention was administered
B: Control group Test Example 8

Guppy Survival Test No. 2

Twenty guppies each which were about 10 days of age after hatching were placed into a fish tank (60 cm×30 cm×30 cm), and fed with a commercially available guppy feed which was mixed with fGH polypeptide of this invention (1 mg/fish of freeze-dried Anacystis nidulans PCC6301old transformant, which corresponded to 1 µg/fish/day of fGH polypeptide of this invention) in amounts of 10 mg/fish/day. Guppies of the control group were reared using, instead of Anacystis nidulans PCC6301old transformant, its non-transformant form. Rearing of guppies was conducted between 25° C. and 27° C. The survival rates between first administration and Day 23 are shown in Table 8 described hereinafter.

TABLE 8

| Day | A (%) | B (%) |
|---|---|---|
| 0 | 100 | 100 |
| 2 | 90 | 90 |
| 6 | 80 | 65 |
| 9 | 70 | 55 |
| 12 | 60 | 40 |
| 16 | 60 | 35 |
| 19 | 60 | 35 |
| 23 | 60 | 35 |

A: Group to which fGH polypeptide of this invention was administered
B: Control group Feed Preparation Example 1

One g of fGH polypeptide expressing Cyanobacterium (freeze-dried), 7 g of a commercially available feed (Swimy, manufactured by Marukyu Co., Ltd.) and 2 g of gluten (manufactured by Marukyu Co., Ltd.) are mixed together and further well mixed after adding water. This mixture is dried in a freeze dryer. After drying, it is smashed into fine pieces in a mortar, and fractionated into, for example, a tube or the like, and stored at −20° C. until use.

Feed Preparation Example 2

Three g of fGH polypeptide expressing Cyanobacterium (freeze-dried) and 7 g of a commercially available feed (Tropical fish food Hikari crest guppy, manufactured by Kyorin Co.) are mixed together and further well mixed after adding water. This mixture is dried in a freeze dryer. After drying, it is smashed into fine pieces in a mortar, fractionated into, for example, a tube or the like, and stored at −20° C. until use.

Feed Preparation Example 3

0.1 g of fGH polypeptide expressing Cyanobacterium (freeze-dried), 7.7 g of a commercially available feed (Swimy, manufactured by Marukyu Co., Ltd.) and 2.2 g of gluten (manufactured by Marukyu Co., Ltd.) are mixed together and further well mixed after adding water. This mixture is dried in a freeze dryer. After drying, it is smashed into fine pieces in a mortar, and then fractionated into, for example, a tube or the like and stored at −20° C. until use.

Feed Preparation Example 4

0.3 g of fGH polypeptide expressing Cyanobacterium (freeze-dried) and 2.7 g of a commercially available feed (Tropical fish food Hikari crest guppy, manufactured by Kyorin Co.) are mixed together and further well mixed after adding water. This mixture is dried in a freeze dryer. After drying, it is smashed into fine pieces in a mortar, and then fractionated into, for example, a tube or the like and stored at −20° C. until use.

Feed Preparation Example 5

A fGH polypeptide containing feed was prepared by adding 0.3 g of freeze-dried *Anacystis nidulans* PCC6301old transformant and water to 19.7 g of a Symphysodon (Discus) feed (manufactured by Tetra Werke Co.), well kneading, and then smashing into fine pieces in a mortar after freeze-drying. The prepared feed was fractionated into, for example, a tube or the like and stored at −20° C. until use.

Feed Preparation Example 6

A fGH polypeptide containing feed was prepared by adding 0.1 g of freeze-dried *Anacystis nidulans* PCC6301old transformant and water to 9.9 g of a Symphysodon (Discus) feed (manufactured by Tetra Werke Co.), well kneading, and then smashing into fine pieces in a mortar after freeze-drying. The prepared feed was fractionated into, for example, a tube or the like and stored at −20° C. until use.

What is claimed is:

1. An isolated polypeptide capable of fish growth promoting activity and comprising the amino acid sequence as set forth in SEQ ID NO:1.

2. The polypeptide as set forth in claim 1, which is purified.

3. An isolated DNA encoding for the polypeptide having SEQ ID NO:1.

4. DNA according to claim 3, which is purified.

5. An isolated DNA comprising the nucleotide sequence as set forth in SEQ ID NO:2.

6. The DNA according to claim 5, which is purified.

7. A fish feed which comprises the polypeptide according to claim 1.

8. A method for growth promotion in fish or reduction in fry mortality, which comprises administering to the fish the polypeptide according to claim 1.

9. A method for preparing a fish feed which comprises blending a fish feed with the polypeptide of claim 1.

10. A vector for expressing a polypeptide capable of fish growth promoting activity, said vector comprising DNA comprising the nucleotide sequence as set forth in SEQ ID NO:2.

11. A vector according to claim 10, wherein the vector is pBAX18fGH.

12. A Cyanobacterium which is transformed by the expression vector according to claim 10.

13. A *Anacystis nidulans* PCC6301old strain which is transformed with pBAX18fGH.

14. A dry bacterial cell of the transformed *Anacystis nidulans* PCC6301old strain according to claim 13 which expresses a polypeptide comprising the amino acid sequence as set forth in SEQ ID NO:1.

15. A fish feed which comprises the dry bacterial cells according to claim 14.

16. A fish feed according to claim 15 which is freeze-dried.

17. A method for growth promotion in fish or reduction in fry mortality which comprises administering to the fish the dry bacterial cells according to claim 14.

18. A method for preparing a fish feed which comprises blending a fish feed with dry bacterial cells according to claim 14.

19. The method of claim 18 further comprising freeze-drying said blend.

* * * * *

SEQUENCE LISTING (1) GENERAL INFORMATION:

(iii) NUMBER OF SEQUENCES:2

(2) INFORMATION FOR SEQ ID NO: 1:

(i) SEQUENCE CHARACTERISTICS:
        (A) LENGTH:187
        (B) TYPE:amino acid
        (C) TOPOLOGY:linear     (ii) MOLECULE TYPE:peptide     (xi) SEQUENCE DESCRIPTION:SEQ ID NO:1:

```
Gln Pro Ile Thr Asp Ser Gln Arg Leu Phe Ser Ile Ala Val Ser Arg
 1               5                  10                  15

Val Gln His Leu His Leu Leu Ala Gln Arg Leu Phe Ser Asp Phe Glu
                20                  25                  30

Ser Ser Leu Gln Thr Glu Glu Gln Arg Gln Leu Asn Lys Ile Phe Leu
                35                  40                  45

Gln Asp Phe Cys Asn Ser Asp Tyr Ile Ile Ser Pro Ile Asp Lys His
            50                  55                  60

Glu Thr Gln Arg Ser Ser Val Leu Lys Leu Leu Ser Ile Ser Tyr Arg
65                  70                  75                  80

Leu Val Glu Ser Trp Glu Phe Pro Ser Arg Ser Leu Ser Gly Gly Ser
                    85                  90                  95

Ala Pro Arg Asn Gln Ile Ser Pro Lys Leu Ser Glu Leu Lys Met Gly
                100                 105                 110

Ile His Leu Leu Ile Arg Ala Asn Gln Asp Gly Ala Glu Met Phe Ala
            115                 120                 125

Asp Ser Ser Ala Leu Gln Leu Ala Pro Tyr Gly Asn Tyr Tyr Gln Ser
        130                 135                 140

Leu Gly Gly Asp Glu Ser Leu Arg Arg Asn Tyr Glu Leu Leu Ala Cys
145                 150                 155                 160

Phe Lys Lys Asp Met His Lys Val Glu Thr Tyr Leu Arg Val Ala Lys
                165                 170                 175

Cys Arg Leu Ser Pro Glu Ala Asn Cys Thr Leu
                180                 185
```

(2) INFORMATION FOR SEQ ID NO: 2:

```
    (i) SEQUENCE CHARACTERISTICS:
        (A) LENGTH:561
        (B) TYPE:nucleic acid
        (C) STRANDEDNESS:double-stranded
        (D) TOPOLOGY:linear (ii) MOLECULE TYPE:synthetic DNA (vi) ORIGINAL SOURCE:
        (A) ORGANISM:

(ix) FEATURE:
        (A) NAME/KEY:

(xi) SEQUENCE DESCRIPTION:SEQ ID NO:2:

cagcctatta ccgattctca gcgtctgttc tctattgctg tttctcgtgt tcagcacctg        60
cacctgctgg cgcagcgtct gttctctgat tttgaatctt ctctgcaaac cgaagaacag       120
cgtcagctga acaaaatttt cctgcaggat ttctgtaact ctgattacat tatttctcct       180
attgataaac acgaaactca gcgttcttct gttctgaaac tgctgtctat ttcttaccgt       240
ctggttgaat cttgggaatt cccttctcgt tctctgtctg gtggttctgc tcctcgtaac       300
cagatttctc ctaaactgtc cgagctcaaa atgggtattc acctgctgat tcgtgctaac       360
caggatggtg ctgaaatgtt cgctgattct tctgctctgc agctcgctcc ttacggtaac       420
tactaccagt ctctgggtgg tgatgaatct ctgcgtcgta actacgaact gctggcttgt       480
ttcaaaaaag atatgcacaa agttgaaacc tacctgcgtg tcgcgaaatg tcgtctgtct       540
cctgaagcta actgcaccct g                                                 561
```